United States Patent
Busacca et al.

(10) Patent No.: US 7,608,614 B2
(45) Date of Patent: Oct. 27, 2009

(54) PROCESS FOR PREPARING MACROCYCLIC COMPOUNDS

(75) Inventors: Carl Alan Busacca, Poughkeepsie, NY (US); Fabrice Gallou, Paris (FR); Nizar Haddad, Danbury, CT (US); Azad Hossain, Glen Allen, VA (US); Suresh R. Kapadia, Danbury, CT (US); Jianxiu Liu, Richmond, VA (US); Chris Senanayake, Brookfield, CT (US); Xudong Wei, Ridgefield, CT (US); Nathan K. Yee, Danbury, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 334 days.

(21) Appl. No.: 11/276,573

(22) Filed: Mar. 6, 2006

(65) Prior Publication Data

US 2006/0205638 A1  Sep. 14, 2006

Related U.S. Application Data

(60) Provisional application No. 60/659,696, filed on Mar. 8, 2005.

(51) Int. Cl.
*A61K 31/47* (2006.01)
(52) U.S. Cl. .................................... 514/187; 514/314
(58) Field of Classification Search ............... 514/187, 514/253.07, 314
See application file for complete search history.

(56) References Cited

U.S. PATENT DOCUMENTS

| | | | |
|---|---|---|---|
| 6,608,027 B1 | 8/2003 | Tsantrizos | |
| 6,867,185 B2 | 3/2005 | Campbell et al. | |
| 7,049,325 B2 * | 5/2006 | Broka et al. | 514/312 |
| 7,173,004 B2 | 2/2007 | McPhee et al. | |
| 7,189,844 B2 | 3/2007 | Gallou et al. | |
| 7,375,218 B2 | 5/2008 | Gallou | |
| 2003/0224977 A1 | 12/2003 | Llinas-Brunet | |
| 2004/0248779 A1 | 12/2004 | Dersch | |
| 2005/0020503 A1 | 1/2005 | Llinas-Brunet et al. | |
| 2005/0049187 A1 | 3/2005 | Brandenburg | |
| 2005/0075279 A1 | 4/2005 | Llinas-Brunet | |
| 2005/0080005 A1 | 4/2005 | Llinas-Brunet | |
| 2005/0153877 A1 | 7/2005 | Miao et al. | |
| 2005/0209135 A1 | 9/2005 | Busacca et al. | |
| 2005/0267018 A1 | 12/2005 | Blatt et al. | |
| 2005/0267151 A1 | 12/2005 | Busacca et al. | |
| 2006/0009667 A1 | 1/2006 | Herweck et al. | |
| 2008/0177029 A1 | 7/2008 | Busacca et al. | |

FOREIGN PATENT DOCUMENTS

| | | |
|---|---|---|
| WO | 03053349 A2 | 7/2003 |
| WO | 2004094452 A2 | 11/2004 |
| WO | 2005095403 A2 | 10/2005 |

OTHER PUBLICATIONS

Saneyoshi, Mineo, Chemical & Pharmaceutical Bulletin (1968), 16(7), 1390-4.*
Wrobel, Zbigniew; Silane-Mediated Direct Condensation of Nitroarenes with Cinnamyl-type Sulfones. The way to 2-Aryl-4-X-quinolines and Their Hetero Analogs;Tetrahedron 54 (1998) 2607-2618.
Jerry March; Advanced Organic Chemistry; 1992; 4th Edition; John Wiley and Sons; XP002385266; pp. 641-644.

* cited by examiner

*Primary Examiner*—David Lukton
(74) *Attorney, Agent, or Firm*—Michael P. Morris; Mary-Ellen M. Devlin; Philip I. Datlow

(57) ABSTRACT

Intermediates of the formula QUIN:

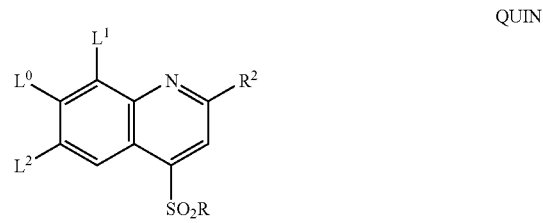

and methods for their preparation are described. The intermediate compounds are useful for preparing active agents for the treatment of hepatitis C virus (HCV) infection.

26 Claims, No Drawings

PROCESS FOR PREPARING MACROCYCLIC COMPOUNDS

This application claims the benefit of U.S. Provisional Application No. 60/659,696, filed on Mar. 8, 2005.

BACKGROUND OF THE INVENTION

1. Technical Field

The invention relates to an improved process for the preparation of macrocyclic compounds useful as agents for the treatment of hepatitis C viral (HCV) infections.

2. Background Information

The macrocyclic compounds of the following formula (I) and methods for their preparation are known from: Tsantrizos et al., U.S. Pat. No. 6,608,027 B1; Llinas Brunet et al, U.S. Application Publication No. 2003/0224977 A1; Llinas Brunet et al, U.S. Application Publication No. 2005/0075279 A1; Llinas Brunet et al, U.S. Application Publication No. 2005/0080005 A1; Brandenburg et al., U.S. Application Publication No. 2005/0049187 A1; and Samstag et al., U.S. Application Publication No. 2004/0248779 A1:

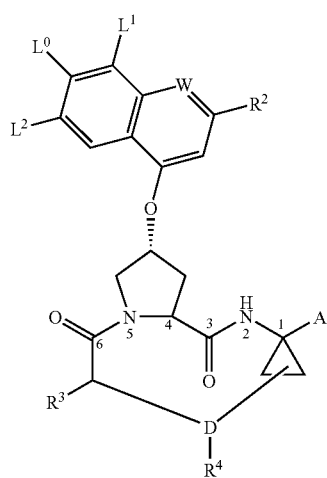

(I)

wherein W is CH or N, $L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$alkyl or $C_{3-6}$cycloalkyl;

$L^1$, $L^2$ are each independently H, halogen, $C_{1-4}$ alkyl, —O—$C_{1-4}$ alkyl, or —S—$C_{1-4}$ alkyl (the sulfur being in any oxidized state); or $L^0$ and $L^1$ or $L^0$ and $L^2$ may be covalently bonded to form together with the two C-atoms to which they are linked a 4-, 5- or 6-membered carbocyclic ring wherein one or two (in the case of a 5- or 6-membered ring) —$CH_2$— groups not being directly bonded to each other, may be replaced each independently by —O— or $NR^a$ wherein $R^a$ is H or $C_{1-4}$alkyl, and wherein said ring is optionally mono- or di-substituted with $C_{1-4}$ alkyl;

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxy-$C_{1-6}$ alkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^6$, wherein $R^6$ is H, halo, $C_{1-6}$alkyl, $C_{3-6}$cycloalkyl, $C_{1-6}$alkoxy, $C_{3-6}$ cycloalkoxy, $NO_2$, $N(R^7)_2$, NH—C(O)—$R^7$; or NH—C(O)—NH—$R^7$ wherein each $R^7$ is independently: H, $C_{1-6}$ alkyl or $C_{3-6}$ cycloalkyl;

or $R^6$ is NH—C(O)—$OR^8$ wherein $R^8$ is $C_{1-6}$ alkyl or $C_{3-6}$ cycloalkyl;

$R^3$ is hydroxy, $NH_2$, or a group of formula —NH—$R^9$, wherein $R^9$ is $C_6$ or $C_{10}$ aryl, heteroaryl, —C(O)—$R^{10}$, —C(O)—$NHR^{10}$ or —C(O)—$OR^{10}$, wherein $R^{10}$ is $C_{1-6}$ alkyl or $C_{3-6}$ cycloalkyl;

D is a 5 to 10-atom unsaturated alkylene chain;

$R^4$ is H, or from one to three substituents at any carbon atom of said chain D, said substituent independently selected from: $C_{1-6}$ alkyl, $C_{1-6}$ haloalkyl, $C_{1-6}$ alkoxy, hydroxy, halo, amino, oxo, thio, and $C_{1-6}$ thioalkyl; and A is an amide of formula —C(O)—NH—$R^{11}$, wherein $R^{11}$ is selected from: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof;

The compounds of formula (I) are disclosed in the above-mentioned patent documents as being active agents for the treatment of hepatitis C virus (HCV) infections. The methods disclosed for the preparation of these compounds include many synthetic steps. The problem addressed by the present invention is to provide a practical and economical process which allows for the efficient manufacture of these compounds with a minimum number of steps and with sufficient overall yield.

BRIEF SUMMARY OF THE INVENTION

It has been discovered that the compounds of formula (I) described above can be prepared more efficiently if the synthesis is carried out using the following key synthetic substitution step wherein a macrocyclic compound of formula (3) is reacted with a sulfonyl-substituted compound of formula QUIN:

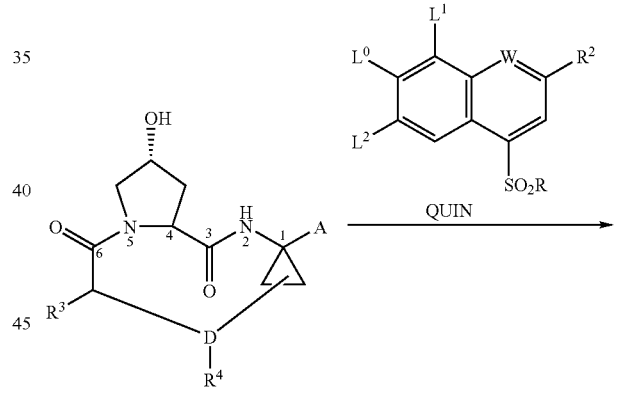

(3)

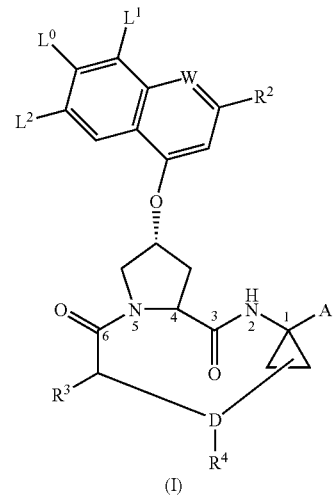

(I)

and when A is a protected carboxylic acid group, optionally subjecting the compound of formula (I) to de-protection conditions to obtain a compound of formula (I) wherein A is a carboxylic acid group;

and when A is a carboxylic acid group in the resulting compound of formula (I), optionally coupling this compound with a sulfonamide of formula $R^{11.4}SO_2NH_2$ in the presence of a suitable coupling agent, such as carbodiimide reagents, TBTU or HATU, to obtain a compound of formula (I) wherein A is $-C(O)-NH-SO_2R^{11.4}$.

In this process there is also no inversion of configuration at the hydroxyl group of the proline moiety which further renders the approach more direct and minimizes problems of stereocontrol, and the quinoline building block is incorporated in the molecule toward the end of the process thus minimizing losses of a costly intermediate.

The present invention is therefore directed to a synthetic process for preparing compounds of formula (I) using the synthetic sequences as described herein; particular individual steps of this process; and particular individual intermediates used in this process.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

The term "$C_{1-6}$ alkyl" as used herein, either alone or in combination with another substituent, means acyclic, straight or branched chain alkyl substituents containing from 1 to six carbon atoms and includes, for example, methyl, ethyl, propyl, butyl, hexyl, 1-methylethyl, 1-methylpropyl, 2-methylpropyl, and 1,1-dimethylethyl.

The term "$C_{3-6}$ cycloalkyl" as used herein, either alone or in combination with another substituent, means a cycloalkyl substituent containing from three to six carbon atoms and includes cyclopropyl, cyclobutyl, cyclopentyl, and cyclohexyl.

The term "unsaturated alkylene chain" as used herein means a divalent alkenyl substituent derived by the removal of one hydrogen atom from each end of a mono- or poly-unsaturated straight or branched chain aliphatic hydrocarbon and includes, for example:

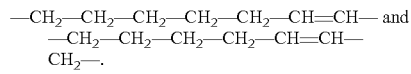

The term "$C_{1-6}$ alkoxy" as used herein, either alone or in combination with another substituent, means the substituent $C_{1-6}$ alkyl-O— wherein alkyl is as defined above containing up to six carbon atoms. Alkoxy includes methoxy, ethoxy, propoxy, 1-methylethoxy, butoxy and 1,1-dimethylethoxy. The latter substituent is known commonly as tert-butoxy.

The term "$C_{3-6}$ cycloalkoxy" as used herein, either alone or in combination with another substituent, means the substituent $C_{3-6}$ cycloalkyl-O— containing from 3 to 6 carbon atoms.

The term "$C_{2-7}$ alkoxy-$C_{1-6}$alkyl" as used herein, means the substituent $C_{2-7}$ alkyl-O—$C_{1-6}$ alkyl wherein alkyl is as defined above containing up to six carbon atoms.

The term "haloalkyl" as used herein means as used herein, either alone or in combination with another substituent, means acyclic, straight or branched chain alkyl substituents having one or more hydrogens substituted for a halogen selected from bromo, chloro, fluoro or iodo.

The term "thioalkyl" as used herein means as used herein, either alone or in combination with another substituent, means acyclic, straight or branched chain alkyl substituents containing a thiol (HS) group as a substituent. An example of a thioalkyl group is a thiopropyl, e.g., HS—$CH_2CH_2CH_2$— is one example of a thiopropyl group.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl ring system.

The term "$C_{7-16}$ aralkyl" as used herein, either alone or in combination with another substituent, means an aryl as defined above linked through an alkyl group, wherein alkyl is as defined above containing from 1 to 6 carbon atoms. Aralkyl includes for example benzyl, and butylphenyl.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

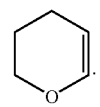

The term "Het" also includes a heterocycle as defined above fused to one or more other cycle be it a heterocycle or a carbocycle, each of which may be saturated or unsaturated. One such example includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic system include: quinoline, indole, pyridine,

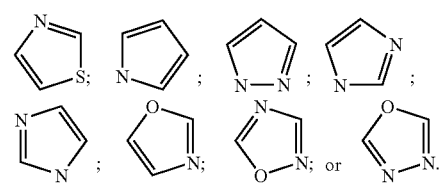

The term "oxo" means the double-bonded group (=O) attached as a substituent.

The term "thio" means the double-bonded group (=S) attached as a substituent.

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

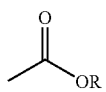

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1-19, incorporated herein by reference).

The following chemicals may be referred to by these abbreviations:

| Abbreviation | Chemical Name |
| --- | --- |
| ACN | Acetonitrile |
| Boc | Tert-butoxylcarbonyl |
| DABCO | 1,4-diazabicyclo[2.2.2]octane |
| DBU | 1,8-Diazabicyclo[5.4.0]undec-7-ene |
| DCC | 1,3-Dicyclohexylcarbodiimide |
| DCHA | Dicyclohexylamine |
| DCM | Dichloromethane |
| DIPEA | Diisopropylethylamine or Hünigs-Base |
| DMAP | Dimethylaminopyridine |
| DMF | N,N-Dimethylformamide |
| DMSO | Dimethylsulfoxide |
| DMTMM | 4-(4,6-Dimethoxy-1,3,5-triazin-2-yl)-4-methylmorpholinium Chloride |
| EDC | 1-(3-dimethylaminopropyl)-3-ethylcarbodiinide hydrocholide |
| HATU | O-(7-azabenzotriazol-1-yl)-N,N,',N'-tetramethyluronium hexafluorophosphate |
| HBTU | O-Benzotriazol-1-yl-N,N,',N'-tetramethyluronium hexafluorophosphate |

-continued

| Abbreviation | Chemical Name |
| --- | --- |
| HOAT | 1-Hydroxy-7-azabenzotriazole |
| HOBT | 1-Hydroxybenzotriazole |
| IPA | Isopropyl alcohol |
| KDMO | Potassium 3,7-dimethyl-3-octanoxide |
| MCH | Methylcyclohexane |
| MIBK | 4-Methyl-2-pentanone |
| NMP | 1-Methyl-2-pyrrolidinone |
| SEH | Sodium 2-ethylhexanoate |
| TBTU | O-(Benzotriazol-1-yl)-N,N,N',N'-tetramethyluronium tetrafluoroborate |
| THF | Tetrahydofuran |
| THP | Trishydroxymethylphosphine |
| TKC | Tetrakis hydroxymethyl phosphonium chloride |

EMBODIMENTS OF THE INVENTION

In the synthetic schemes below, unless specified otherwise, all the substituent groups in the chemical formulas shall have the same meanings as in the Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in the International Patent Applications WO 00/59929, WO 00/09543 and WO 00/09558, U.S. Pat. No. 6,323,180 B1 and U.S. Pat. No. 6,608,027 B1.

Optimum reaction conditions and reaction times may vary depending on the particular reactants used. Unless otherwise specified, solvents, temperatures, pressures, and other reaction conditions may be readily selected by one of ordinary skill in the art to obtain optimum results for a particular reaction. Typically, reaction progress may be monitored by High Pressure Liquid Chromatography (HPLC), if desired, and intermediates and products may be purified by chromatography on silica gel and/or by recrystallization.

I. General Multi-Step Synthetic Method

In one embodiment, the present invention is directed to a general multi-step synthetic method for preparing the compounds of formula (I). Specifically, this embodiment is directed to a process for preparing a compound of the following formula (I):

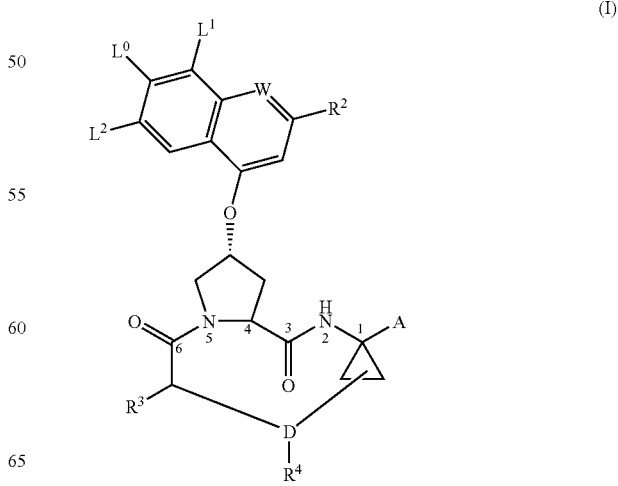

(I)

wherein W is CH or N,

L⁰ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$L^1$, $L^2$ are each independently H, halogen, $C_{1-4}$alkyl, —O—$C_{1-4}$alkyl, or —S—$C_{1-4}$alkyl (the sulfur being in any oxidized state); or $L^0$ and $L^1$ or $L^0$ and $L^2$ may be covalently bonded to form together with the two C-atoms to which they are linked a 4-, 5- or 6-membered carbocyclic ring wherein one or two (in the case of a 5- or 6-membered ring) —CH₂— groups not being directly bonded to each other, may be replaced each independently by —O— or $NR^a$ wherein $R^a$ is H or $C_{1-4}$alkyl, and wherein said ring is optionally mono- or di-substituted with $C_{1-4}$ alkyl;

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxy-$C_{1-6}$ alkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;

or $R^6$ is NH—C(O)—$OR^8$ wherein $R^8$ is $C_{1-6}$ alkyl or $C_{3-6}$ cycloalkyl;

$R^3$ is hydroxy, $NH_2$, or a group of formula —NH—$R^9$, wherein $R^9$ is $C_6$ or $C_{10}$ aryl, heteroaryl, —C(O)—$R^{10}$, —C(O)—$NHR^{10}$ or —C(O)—$OR^{10}$, wherein $R^{10}$ is $C_{1-6}$ alkyl or $C_{3-6}$ cycloalkyl;

D is a 5 to 10-atom unsaturated alkylene chain;

$R^4$ is H, or from one to three substituents at any carbon atom of said chain D, said substituent independently selected from: $C_{1-6}$ alkyl, $C_{1-6}$ haloalkyl, $C_{1-6}$ alkoxy, hydroxy, halo, amino, oxo, thio, and $C_{1-6}$ thioalkyl; and A is an amide of formula —C(O)—NH—$R^{11}$, wherein $R^{11}$ is selected from: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof;

said process comprising the following steps:

(i) when R=PG and PG is a protecting group, cyclizing a diene compound of formula (1) in the presence of a suitable catalyst to obtain a compound of formula (2) and subsequently subjecting the compound of formula (2) to de-protection conditions to obtain a compound of formula (3); or when R=H, cyclizing a diene compound of formula (1) in the presence of a suitable catalyst to obtain a compound of formula (3):

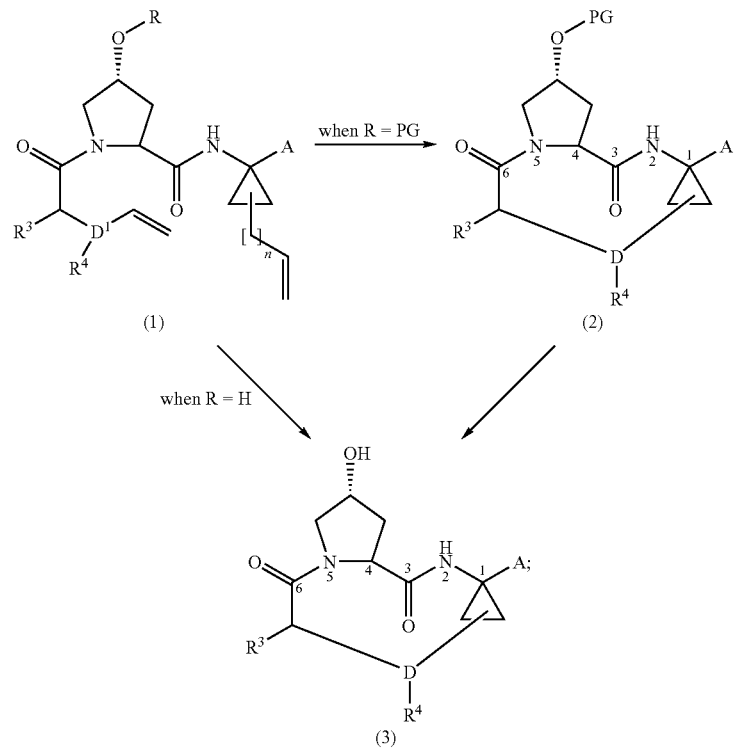

wherein A, D, $R^3$ and $R^4$ are as defined for formula (I) above, R is hydrogen or PG wherein PG is a protecting group, n is an integer from 0 to 2, and $D^1$=D-(n+2);

(ii) when A is a protected carboxylic acid group in formula (3), optionally subjecting the compound of formula (3) to de-protection conditions to obtain a compound of formula (3) wherein A is a carboxylic acid group; and (iii) reacting a compound of formula (3) with a compound of formula QUIN, wherein $R^3$, $R^4$, D, A, $L^0$, $L^1$, $L^2$, W and $R^2$ are as defined for formula (I) above, and R is $C_{1-6}$alkyl, $C_6$ or $C_{10}$ aryl or heteroaryl, to obtain a compound of formula (I):

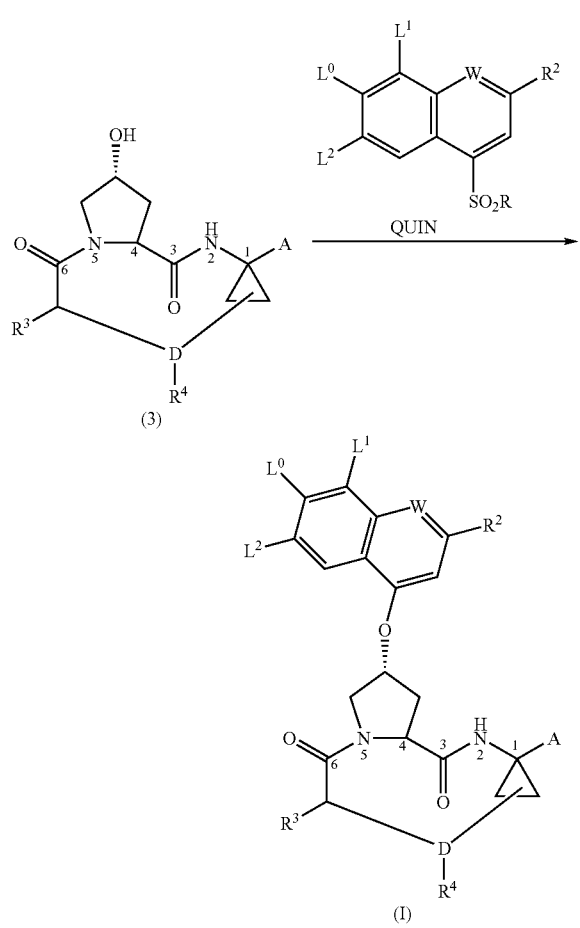

and when A is a protected carboxylic acid group in formula (I), optionally subjecting the compound of formula (I) to de-protection conditions to obtain a compound of formula (I) wherein A is a carboxylic acid group;

and when A is a carboxylic acid group in the resulting compound of formula (I), optionally coupling this compound with a sulfonamide of formula $R^{114}SO_2NH_2$ in the presence of a suitable coupling agent, such as carbodiimide reagents, TBTU or HATU, to obtain a compound of formula (I) wherein A is —C(O)—NH—$SO_2R^{114}$.

II. The Individual Steps of the Synthetic Method

Additional embodiments of the invention are directed to the individual steps of the multistep general synthetic method described above and the individual intermediates used in these steps. These individual steps and intermediates of the present invention are described in detail below. All substituent groups in the steps described below are as defined in the general multi-step method above.

Step (i)

This step is directed to cyclizing a diene compound of formula (1) in the presence of a suitable catalyst to obtain a compound of formula (2) when R=a protecting group and subsequently subjecting the compound of formula (2) to de-protection conditions to obtain a compound of formula (3); or when R=H, cyclizing a diene compound of formula (1) in the presence of a suitable catalyst to directly obtain a compound of formula (3):

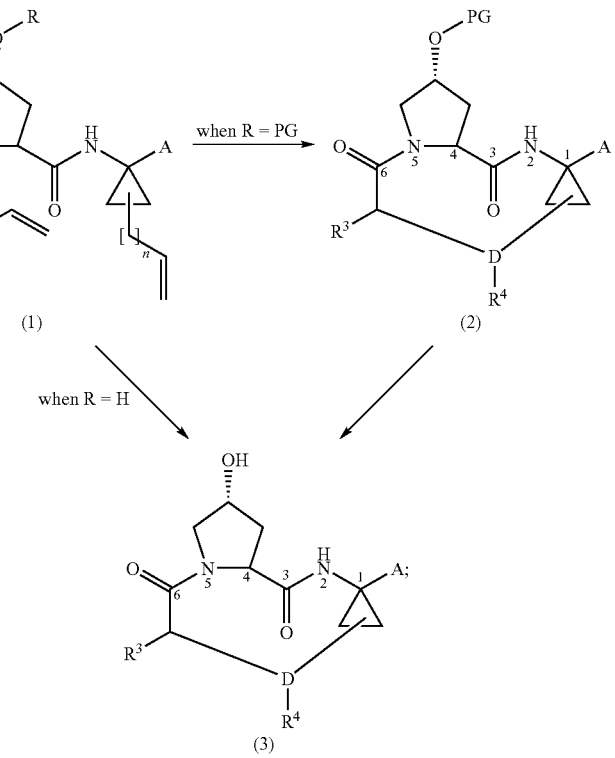

Suitable ring-closing catalysts for this cyclization step include ruthenium based catalysts, as well as the commonly used molybdenum-based (Schrock and modified Schrock catalysts) and tungsten-based catalysts. For example, any of the well-known ruthenium based catalysts used in olefin metathesis reactions, such as Grubb's catalyst (first and second generation), Hoveyda's catalyst (first and second generation) and Nolan's catalyst, may be used with appropriate adjustment of reaction conditions as may be necessary to allow ring-closing to proceed, depending upon the particular catalyst that is selected.

Suitable ruthenium catalysts for the cyclization step include, for example, the compounds of formula A, B, C, D or E:

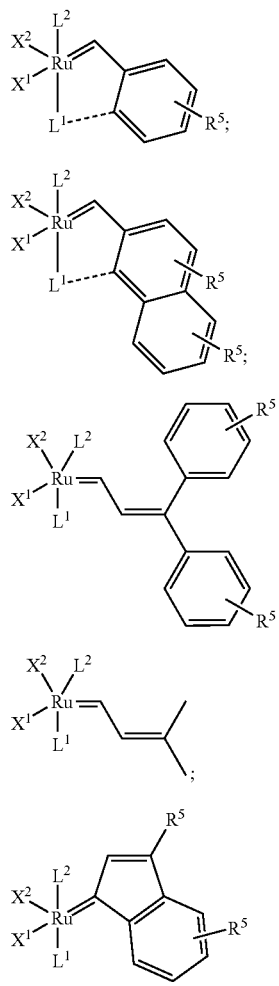

wherein $X^1$ and $X^2$ each independently represent an anionic ligand, $L^1$ represents a neutral electron donor ligand which is bonded to the ruthenium atom and is optionally bonded to the phenyl group, and $L^2$ represents a neutral electron donor ligand which is bonded to the ruthenium atom;

and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl; and wherein $X^2$ and $L^2$ may optionally together form a chelating bidentate ligand.

In a more specific embodiment, the ruthenium catalyst is a compound of formula (A-1) or (A-2):

(A-1)

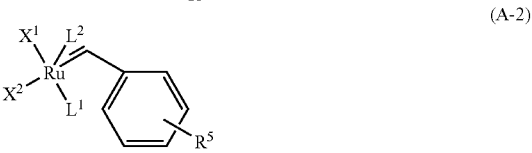

(A-2)

wherein:

$L^1$ is a trisubstituted phosphine group of the formula $PR_3$, wherein R is selected from $C_{1-6}$alkyl and $C_{3-8}$-cycloalkyl, $L^2$ is a trisubstituted phosphine group of the formula $PR_3$, wherein R is selected from $C_{1-6}$alkyl and $C_{3-8}$-cycloalkyl, or $L^2$ is a group of the formula A or B:

(A)

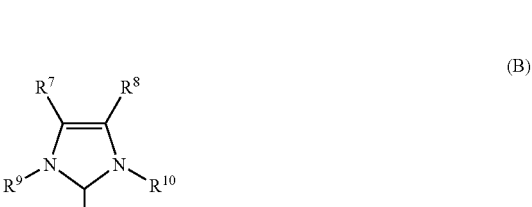

(B)

wherein $R^7$ and $R^8$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and $R^9$ and $R^{10}$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl;

$X^1$ and $X^2$ each independently represent a halogen atom;

$R^5$ represent hydrogen or nitro; and $R^6$ represents a $C_{1-6}$ alkyl group.

In another more specific embodiment, the ruthenium catalyst is selected from:

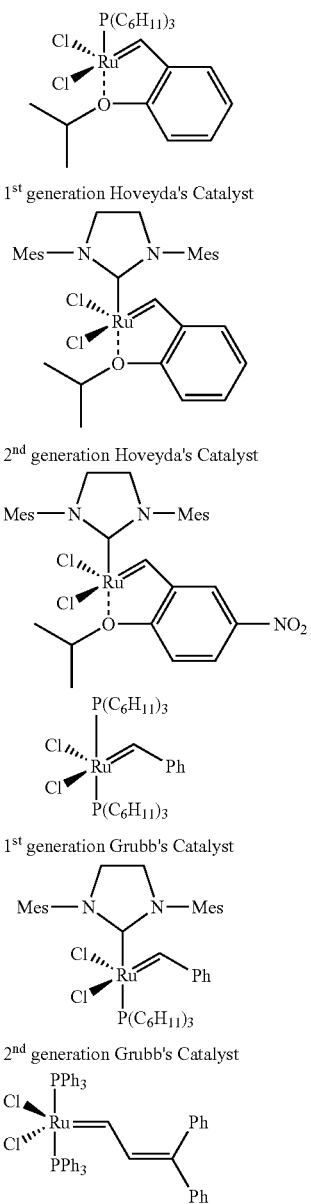

1st generation Hoveyda's Catalyst

2nd generation Hoveyda's Catalyst

1st generation Grubb's Catalyst

2nd generation Grubb's Catalyst where Ph is phenyl and Mes is 2,4,6-trimethylphenyl.

Ruthenium-based catalysts useful for the metathesis cyclization step, such as those set forth above, are all known catalysts that may be obtained by known synthetic techniques. For example, see the following references for examples of suitable ruthenium-based catalysts:

Organometallics 2002, 21, 671; 1999, 18, 5416; and 1998, 17, 2758;

J. Am. Chem. Soc. 2001, 123, 6543; 1999, 121, 791; 1999, 121, 2674; 2002, 124, 4954; 1998, 120, 2484; 1997, 119, 3887; 1996, 118, 100; and 1996, 118, 9606

J. Org. Chem. 1998, 63, 9904; and 1999, 64, 7202;

Angew. Chem. Int. Ed. Engl. 1998, 37, 2685; 1995, 34, 2038; 2000, 39, 3012 and 2002, 41, 4038;

U.S. Pat. Nos. 5,811,515; 6,306,987 B1; and 6,608,027 B1

In another specific embodiment of the present invention the ring-closing reaction is carried out in a solvent at a temperature in the range of from about 20° to about 120° C., Any solvent that is suitable for the ring closing metathesis reaction may be used. Examples of suitable solvents include alkanes, such as n-pentane, n-hexane or n-heptane, aromatic hydrocarbons, such as benzene, toluene or xylene, chlorinated hydrocarbons such as dichloromethane, trichloromethane, tetrachloromethane or dichloroethane, tetrahydrofuran, 2-methyl-tetrahydrofuran, 3-methyl-tetrahydrofuran, cyclopentyl methyl ether, methyl tert-butyl ether, dimethyl ether, methyl alcohol, dioxane, ethyl acetate and tert-butyl acetate.

In another specific embodiment of the present invention the ring-closing reaction is carried out wherein the molar ratio of the diene compound (1) to the catalyst ranges from 1000:1 to 100:1, preferably from 500:1 to 110:1, in particular from 250:1 to 150:1.

In another specific embodiment of the present invention the ring-closing reaction is carried out at a ratio of the diene compound (1) to solvent in the range from 1:400 by weight to 1:25 by weight, preferably from 1:200 by weight to 1:50 by weight, in particular from 1:150 by weight to 1:75 by weight.

In another specific embodiment of the present invention the ring-closing reaction is carried out by portionwise addition of the catalyst in the range from 2 to 6 portions, preferably from 3-5 portions.

One skilled in the art can readily optimize the cyclization step by selecting and adjusting appropriate conditions suitable for the particular ring-closing catalyst selected. For example, depending upon the catalyst selected it may be preferable to run the cyclization step at high temperature, e.g., higher than 90° C., although lower temperatures may also be possible with the addition of an activator such as copper halide (CuX, where X is halogen) to the reaction mixture.

In a particular embodiment of this step, the compound of formula (1) is dissolved in a degassed organic solvent (such as toluene or dichloromethane) to a concentration below about 0.02M, then treated with a ruthenium-based catalyst such as Hoveyda's catalyst, at a temperature from about 40° C. to about 110° C. until completion of the reaction. Some or all of the ruthenium metal may be removed from the reaction mixture by treatment with a suitable heavy metal scavenger, such as THP or other agents known to scavenge heavy metals. The reaction mixture is then washed with water and the organic layer separated and washed. The resulting organic solution may be decolorized, such as by the addition of activated charcoal with subsequent filtration.

In one embodiment, the proline ring oxygen atom in formula (1) has been protected with a protecting group (where R═PG) at any time prior to the cyclization step using conventional techniques. Any suitable oxygen protecting group may be used including, for example, acetate, benzoate, para-nitro benzoate, naphthoates, halogenoacetate, methoxyacetate, phenyl acetate, phenoxy acetate, pivaloate, crotonate, methyl carbonate, methoxymethyl carbonate, ethyl carbonate, halogeno carbonate, para-nitro phenyl carbonate, triisopropyl silyl, triethyl silyl, dimethylisopropyl, diethylisopropyl, dimethylthexylsilyl, t-butyldimethylsilyl, t-butyldiphenylsilyl, tribenzylsilyl, triphenylsilyl, diphenylmethylsilyl, di-t-butylmethylsilyl, tris(trimethylsilyl)silyl, t-butoxymethoxyphenylsilyl, t-butoxydiphenylsilyl, etc. Following the cyclization step, the protecting group PG in compound (2) is removed using conventional de-protection conditions suitable for the particular protecting group, as would be readily understood by one skilled in the art, to obtain compound (3).

In another embodiment, it may be desirable to purify the solution of diene compound of formula (1) prior to the methathesis cyclization step to remove any impurities from the reaction mixture that might inhibit the cyclization reaction. Conventional purification procedures well known to those skilled in this art may be employed. In one preferred embodiment, the solution of diene compound is purified by treatment with alumina, for example, activated alumina, prior to its use in the cyclization step.

Step (ii)

When A is a protected carboxylic acid group in formula (3), e.g. a carboxylic acid ester group, the compound of formula (3) can optionally be subjected to de-protection (hydrolysis) conditions to obtain the corresponding free carboxylic acid compound prior to the next step. Hydrolysis can be carried out using conventional hydrolysis conditions known in the art. In a particular embodiment, for example, an esterified compound of formula (3) is dissolved in an organic solvent such as THF, and a suitable hydrolyzing agent such as lithium hydroxide monohydrate ($LiOH.H_2O$) or sodium hydroxide (NaOH) is added followed by the addition of water. The resultant solution is stirred at a temperature from about 35° C. to about 50° C. At the end of the reaction, the solution is cooled, and the organic layer collected. A suitable solvent such as ethanol is added to the organic layer and the pH is adjusted to from about pH 5 to about pH 6. The mixture is then warmed to a temperature from about 40° C. to about 50° C. at which point water is added and solution is stirred whereupon the compound of formula (3) begins to precipitate. Upon completion of the precipitation, the solution is cooled to ambient temperature and the compound of formula (3) is collected by filtration, washed and dried.

Step (iii)

This step is directed to a process for preparing a compound of formula (I), comprising reacting a compound of formula (3) with a compound of formula QUIN to obtain a compound of formula (I):

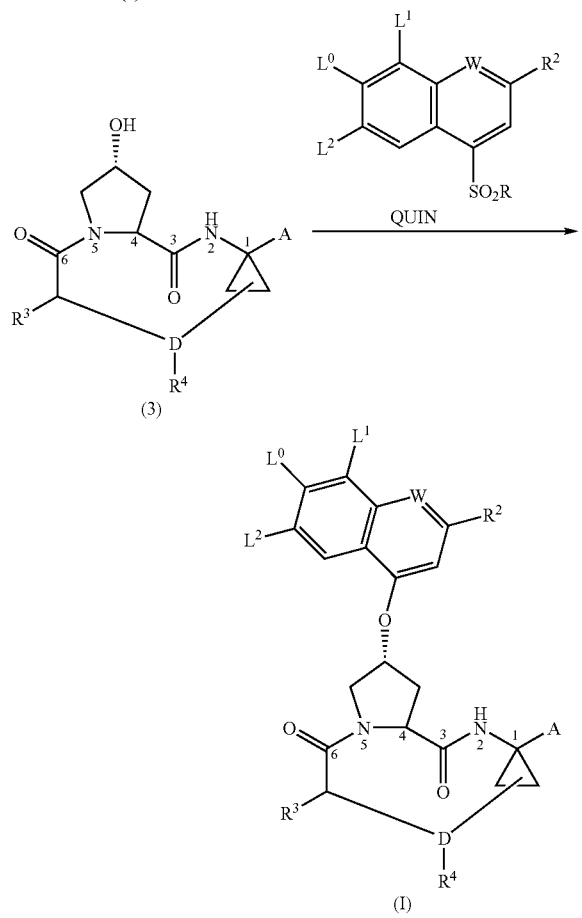

and when A is a protected carboxylic acid group, optionally subjecting the compound of formula (I) to de-protection conditions to obtain a compound of formula (I) wherein A is a carboxylic acid group;

and when A is a carboxylic acid group in the resulting compound of formula (I), optionally coupling this compound with a sulfonamide of formula $R^{114}SO_2NH_2$ in the presence of a suitable coupling agent, such as carbodiimide reagents, TBTU or HATU, to obtain a compound of formula (I) wherein A is —C(O)—NH—$SO_2R^{114}$.

R groups on the sulfonyl group in QUIN include, for example, $C_{1-6}$alkyl, $C_6$ or $C_{10}$ aryl or heteroaryl. A preferred R group is phenyl.

The coupling reaction between the compounds of formulas (3) and QUIN is typically preformed in the presence of a base in a suitable solvent or solvent mixture. Examples of suitable bases for this reaction include t-BuOK, t-BuONa, t-BuOCs, sodium bis(trimethylsilyl)amide, and KDMO, with t-BuOK and KDMO being preferred bases. Examples of suitable solvents for this reaction include polar aprotic solvents, for example, DMSO, DMF, NMP or other common polar aprotic solvents, as well as THF and other moderately polar ethers, or suitable mixtures of these solvents. A preferred solvent is DMSO.

The preferred temperature would be between 0° C. and 50° C. (depending upon solvent freezing points), and most preferably between 10° C. and 25° C.

In yet another preferred embodiment of this step, the following set of reaction conditions may be employed: A flask is charged with the macrocycle (3) and the quinoline QUIN, purged with nitrogen (3 times), then DMSO is added via syringe. The mixture is again purged with nitrogen (3 times), and the temperature adjusted to 20° C. To the slurry is then added 50% KDMO/heptane via syringe pump over 1 hour. The resulting mixture is stirred under nitrogen at ~20° C. for 2 h. The mixture is then quenched by the dropwise addition of glacial HOAc, and the mixture is stirred. The reaction mixture is then slowly added to water, to cause product precipitation. The slurry is then stirred, filtered, and the cake washed with water, then hexanes, and the solid dried.

When A is a protected carboxylic acid group in formula (I), e.g. a carboxylic acid ester group, the compound of formula (I) can optionally be subjected to de-protection (hydrolysis) conditions to obtain the corresponding free carboxylic acid compound. Hydrolysis can be carried out using conventional hydrolysis conditions known in the art. Suitable conditions are the same as discussed previously for step (ii). In addition, when A is a carboxylic acid group in the resulting compound of formula (I), this compound may be coupled with a sulfonamide of formula $R^{114}SO_2NH_2$ in the presence of a suitable coupling agent, such as carbodiimide reagents, TBTU or HATU, to obtain a compound of formula (I) wherein A is —C(O)—NH—$SO_2R^{114}$.

III. Preparation of Peptidic Diene Starting Material

The peptidic diene starting material (1) employed in the above schemes may be synthesized from known materials using the procedures as outlined in the Schemes I to III below.

SCHEME I-PREPARATION OF P2-P1

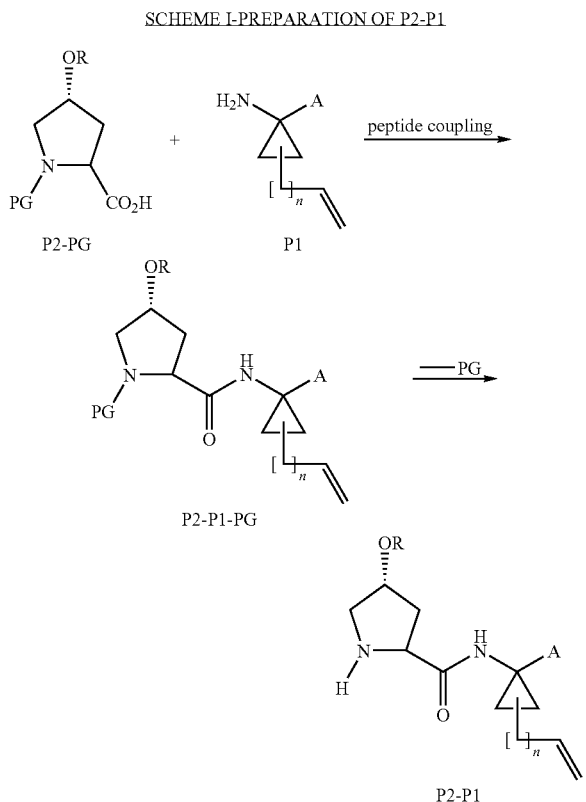

The peptide coupling to give P2-P1-PG, wherein PG is an amino-protecting group, in Scheme I could be performed using any of the conventional peptide coupling reagents and protocols known in the art, and the amino-protecting group PG can be any suitable amino-protecting group that is well known in the art. See, for example, the intermediates and coupling techniques disclosed in WO 00/09543, WO 00/09558 and U.S. Pat. No. 6,608,027 B1. Peptide coupling between compounds of formula P2-PG and P1 could be achieved, for example, under a variety of conditions known in the art using conventional peptide coupling reagents such as DCC, EDC, TBTU, HBTU, HATU, DMTMM, Cyanuric chloride (CC), tosyl chloride (TsCl), mesyl chloride (MsCl), isobutyl chloroformate (IBC), HOBT, or HOAT in aprotic solvents such as dichloromethane, chloroform, THF, DMF, NMP, DMSO.

The next step of cleaving the nitrogen protecting group in the compound of formula P2-P1-PG can also be accomplished by well known techniques, e.g., as described in 00/09543, WO 00/09558 and U.S. Pat. No. 6,608,027 B1. In particular embodiments, this process involves the acid hydrolysis of the compound of formula P2-P1-PG with an organic or inorganic acid, such as HCl, $H_2SO_4$, TFA, AcOH, $MeSO_3H$, in a variety of protic or polar nonprotic solvents such as alcohols, ethers, ACN or DCM.

The compounds of formula P2-PG used as starting material are either commercially available, e.g., Boc-4(R)-hydroxyproline, or can be prepared from known materials using conventional techniques. In one example, the compounds of formula P2-PG where R is hydrogen and PG is an amino-protecting group may be prepared by amino-protection of 4-hydroxyproline:

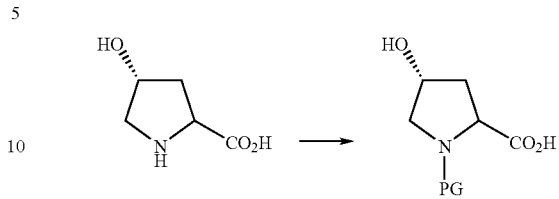

In the first step, an appropriate amino-protecting group is introduced onto the ring nitrogen atom of the 4-hydroxyproline compound using conventional procedures. For example, the compound may be dissolved in a suitable solvent and reacted with an appropriate amino-protecting group introducing reagent. For example, and not intending to be limited in its scope, when Boc (tert-butyloxycarbonyl) is the desired protecting group, the compound is reacted with the anhydride $Boc_2O$ (or Boc-ON) in a solvent mixture such as Acetone/Water, MIBK/Water or THF/Water to which a base such as NaOH, KOH, LiOH, triethylamine, diisopropylethylamine, or N-methyl-pyrrolidine is added, the reaction being carried out at a temperature between 20-60° C.

The compounds of formula P1 are known from WO 00/09543, WO 00/09558 and U.S. Pat. No. 6,608,027 B1, and may be prepared by techniques as described therein.

SCHEME II-PREPARATION OF P3-P2

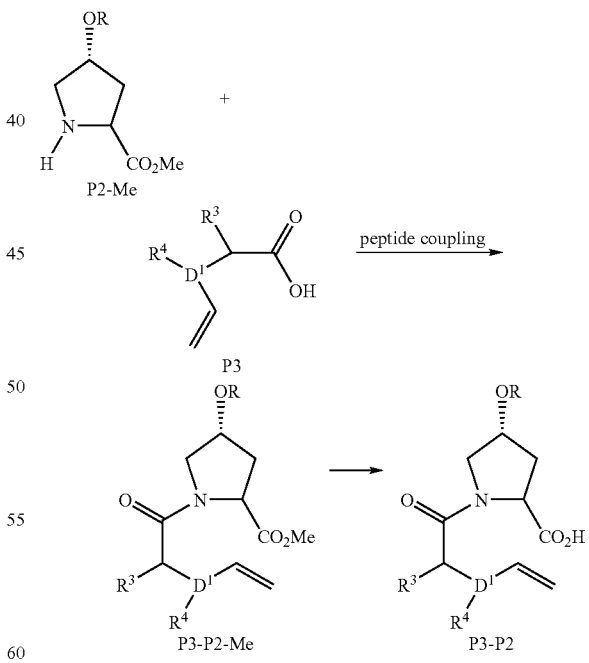

The peptide coupling to give P3-P2-Me in Scheme II could be performed using any of the conventional peptide coupling reagents and protocols known in the art. Examples of suitable reagents and conditions are outlined above with respect to peptide coupling step of Scheme I.

The subsequent hydrolysis to give P3-P2 in Scheme II would be performed with an aqueous basic solution, optionally containing a co-solvent that is miscible with $H_2O$ such as THF, dioxane, alcohols, or DME or combinations of these co-solvents. The preferred solvent mixture would be aqueous base containing THF as a co-solvent. Any water soluble base could be used such as LiOH, NaOH, KOH, $Na_2CO_3$, $K_2CO_3$, and the like. The preferred base would be LiOH. The amount of base could vary from 1 to 100 equivalents with 1-10 equivalents being preferred. The concentration of base could range from 0.25 M to 12 M, with 1-4 M being preferred. The reaction temperature could vary from −40° C. to 100° C., with −20° C. to 50° C. being preferred.

A one-pot sequence for the peptide coupling of P3 with P2-Me can be carried out using CC or an alkyl- or arylsulfonyl chloride (e.g., TsCl, MsCl) under coupling conditions, to form P3-P2-Me followed by hydrolysis of the product by the addition of an aqueous basic solution to provide the compound P3-P2 of Scheme II which may then be crystallized. In this one-pot sequence, the P3 compound can also be used in the form of its salt with a sterically hindered secondary amine, such as its DCHA salt.

The substituted acid compound of formula P3 used as a starting material are known from U.S. Pat. No. 6,608,027 B1 and may be obtained from commercially available materials using the techniques as described therein.

SCHEME III-PREPARATION OF (1)

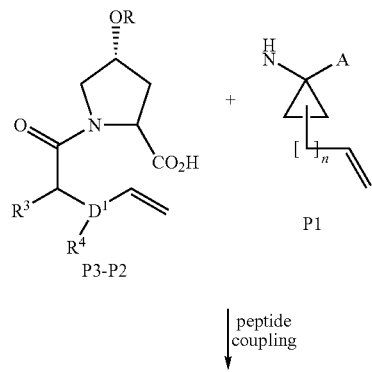

P3-P2 + P1

| peptide coupling

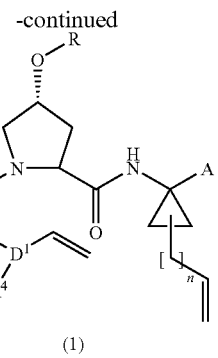

(1)

↑ peptide coupling

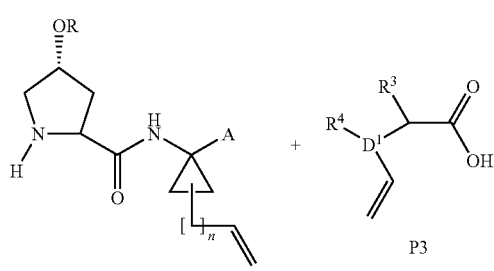

P2-P1 + P3

The peptide couplings to give compound (1) in Scheme III could be performed using any of the conventional peptide coupling reagents and protocols known in the art. Examples of suitable reagents and conditions are outlined above with respect to peptide coupling step of Scheme I. IBC is a preferred peptide coupling reagent for Scheme III.

IV. Preparation of Sulfonated Quinoline Starting Material

The sulfonated quinoline starting material QUIN can be prepared from known materials according to the procedure outlined in Scheme IV below:

SCHEME IV

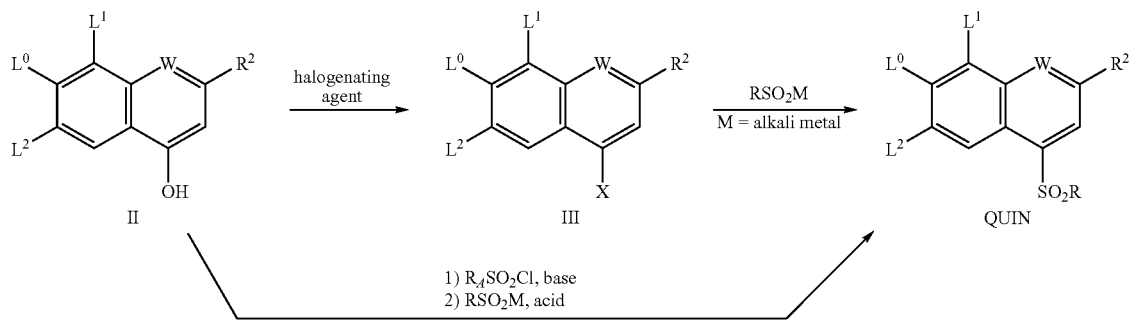

These hydroxyl-substituted quinolines II can be converted to sulfonequinolines QUIN by first converting them to a haloquinoline compound III (where X is halogen) by following well known halogenation procedures using various halogenating reagents such as the commonly used $POX_3$ and $PX_5$, where X=F, Cl, Br or I, wherein these reagents can be used in some cases as solvents or in combination with polar aprotic solvents, such as DMF or Acetonitrile; and then converting halogenated compound III to the target sulfonequinoline QUIN by reaction with a sulfinate salt $RSO_2M$ wherein M is an alkali metal, such as $PhSO_2Na$.

Alternatively, II can be converted to the sulfonequinoline in a one-pot procedure by first generating an intermediate sulfonate by reaction with an arene sulfonylchloride compound $R_4SO_2Cl$ wherein $R_4$ is a neutral or electron rich arene group, such as benzenesulfonyl chloride or tosyl chloride, in the presence of a suitable base in a sutiable solvent. Suitable bases for this step include tertiary amine bases such as N-methylpyrrolidine and diisopropylethylamine, and suitable solvents include aprotic solvents such as acetonitrile, THF, toluene and DMF, preferably acetonitrile. The resulting species is then reacted in situ, under acidic conditions (for example in the presence of acetic, trifluoroacetic, hydrochloric acid or the like, preferably acetic acid), with a sulfinate salt $RSO_2M$ wherein M is an alkali metal, such as $PhSO_2Na$, $PhSO_2K$ or $PhSO_2Cs$, at a suitable reaction temperature, for example in the range of 0 to 100° C., preferably 25 to 50° C. The sulfonequinoline product can be isolated from the reaction mixture using conventional techniques well know to those skilled in the art. In one embodiment, the sulfonequinoline can be crystallized out by cooling the solution to room temperature and adding water. The crystallized product can then be filtered, rinsed and washed using conventional techniques.

The hydroxyl-susbtituted quinoline compounds of formula (II) can be synthesized from commercially available materials using the techniques described in, e.g. from WO 00/59929, WO 00/09543 and WO 00/09558, U.S. Pat. No. 6,323,180 B1, U.S. Pat. No. 6,608,027 B1 and U.S. Application Publication No. 2005/0020503 A1.

An alternative procedure for preparing certain hydroxyl-susbtituted quinoline compounds of formula (II) and their halogenation to a comound of formula (III) is set forth in Scheme V below (in which compound 7 is an example of a compound (II) and compound 8 is an example of a compound (III):

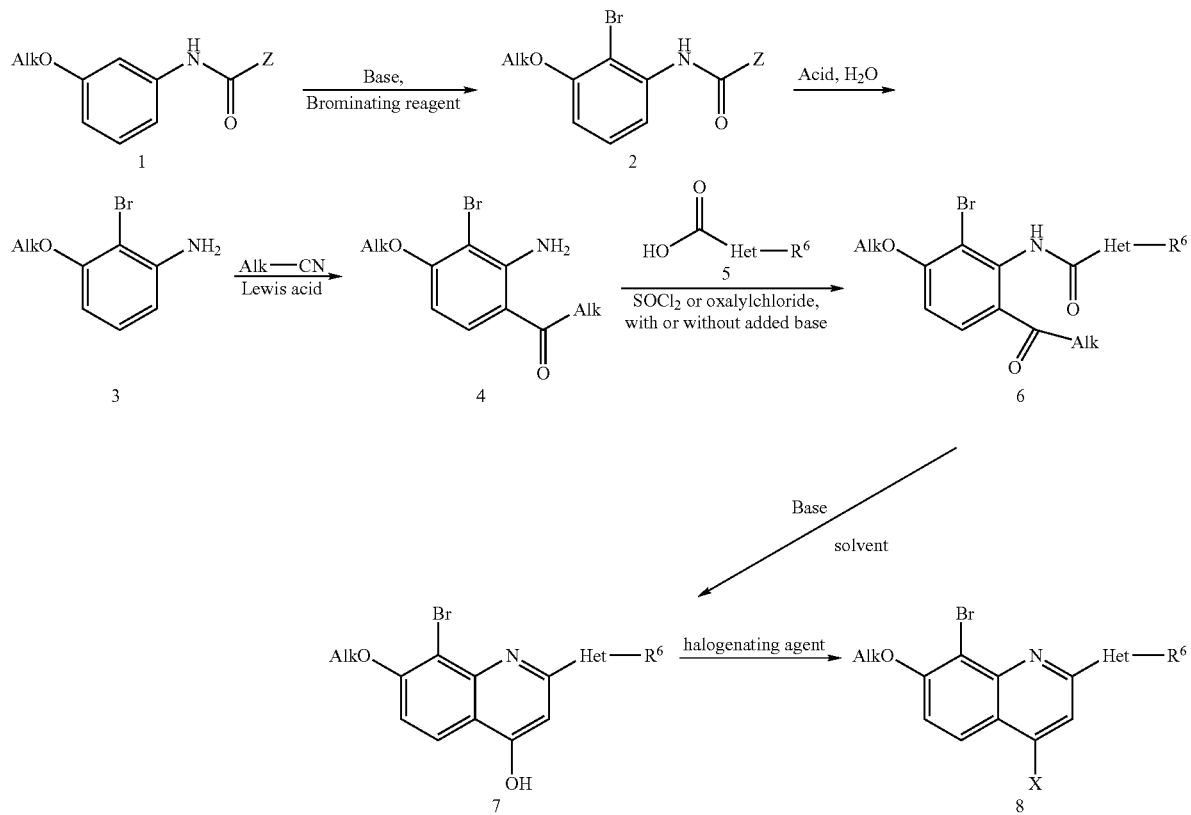

wherein each Alk is independently a $C_1$-$C_6$ alkyl group, X is a halogen atom, Z is tert-butyl or t-butyl-oxy, and $R^6$ and Het are as defined for Formula I.

In the first step, a compound of formula 1 is treated with a base and a brominating agent to obtain compound 2. The general requirements for this step are the use of a base of strength sufficient to form the desired dianion. This could be any alkyllithium, a metalloamide such as Lithium diisopropylamide (LDA), Lithium tetramethylpiperidide, a metallohexamethyldisilazide such as KHMDS, an organozincate, a metal alkoxide in a cation-solvating solvent such as DMSO, and the like. The preferred bases would be n-Butyllithium and LDA. Any organic solvent that does not interfere with the dianion formation could be used, such as THF, alkyl-THF's, dioxane, alkanes, cycloalkanes, dialkylethers such as MTBE, cyclopentylmethylether, dibutylether, and the like. The preferred solvents would be THF, alkyl-THF's and alkanes. The temperature for the dianion formation could be between −100° C. and 25° C., with the preferred range between −30° C. and 25° C. The brominating reagent could be any compound which contains a labile bromine atom such as $Br_2$, NBS, bromohydantoins, N-bromophthalimides, bromohaloalkanes such as 1,2-dibromotetrachloroethane and perfluoroalkylbromides, and the like. The preferred brominating reagents would be the bromohaloalkanes. Once the dianion has been generated in a suitable solvent, the brominating reagent could be added neat or in solution, or alternatively the dianion could be added to the brominating reagent either neat or in solution. The preferred mode would be to add the dianion slowly to the brominating reagent in solution. The temperature for the bromination could be between −100° C. and 25° C., with the preferred range between −30° C. and 25° C.

In the next step, compound 2 is hydrolyzed by treatment with an aqueous acid mixture to obtain 3. Any aqueous acid mixture could be used such as water with [trifluoroacetic acid, a chloroacetic acid such as trichloroacetic acid, a sulfonic acid such as methanesulfonic acid, hydrochloric acid, sulfuric acid, nitric acid, phosphoric acid, a strong acid resin such as DOWEX 50], and the like. The preferred acids would be hydrochloric acid and sulfuric acid in 2-12 M concentration, preferably at least 6M. Cosolvents that are miscible with water could also be used, such as alcohols like ethanol, isopropanol, or ethers such as DME, diglyme, and the like. The hydrolysis could be carried out between 0° C. and 200° C., with the preferred temperature between 0° C. and 100° C.

In the next step, compound 3 is treated with an alkylated nitrile (Alk—CN) and a Lewis acid to obtain compound 4. For the conversion of 3 to 4, Lewis acids by themselves or in combination, could be used, such as $AlCl_3$, $BCl_3$, $GaCl_3$, $FeCl_3$ and mixtures thereof, and the like. The preferred method would be to use $BCl_3$ with $AlCl_3$. Any solvent which will not be easily acylated could be used such as halocarbons, halobenzenes, alkylbenzenes such as toluene, and alkylnitriles such as acetonitrile, with the preferred solvents being 1,2-dichloroethane, chlorobenzene and toluene. The reaction temperature could be between 0° C. and 150° C., preferably between 25° C. and 75° C.

In the next step, compound 4 is acylated with compound 5 to obtain compound 6. For the conversion of 4 to 6, acylation could be achieved by either first converting carboxylic acid 5 to an activated form such as an acid chloride or by using standard peptide coupling protocols. The preferred method would be to create the acid chloride of compound 5 using oxalyl chloride or thionyl chloride. This activated species would then be coupled with aniline 4 in any organic solvent or in water, with or without an added base. The preferred solvents would be NMP and THF and the preferred base (if used) is triethylamine. The reaction temperature could be between −30° C. and 150° C., preferably between −20° C. and 50° C.

In the next step, compound 6 is cyclized in the presence of a base to obtain compound 7. Compound 6 can be isolated and purified, or alternatively, crude 6 in an organic solvent such as NMP can simply be subjected to the cyclization conditions to furnish quinolone 7 directly, preforming two steps in a one-pot process. For the conversion of 6 to 7 in Scheme I, any base capable of forming the enolate could be used, such as t-BuOK, KDMO, LDA, and the like, with t-BuOK and KDMO being preferred. Any organic solvent which does not react with the enolate could be used, such as THF's, dioxane, DMSO, NMP, DME, and the like, with NMP, DME and DMSO being preferred. The cyclization could be performed at any temperature between 25° C. and 150° C., with 50° C. to 100° C. being preferred.

In the final step, hydroxoquinoline compound 7 is treated with a halogenating agent to obtain the compound 8. For the conversion of 7 to 8 in Scheme I, many halogenating reagents could be used, such as methanesulfonyl chloride, $SOCl_2$, $POCl_3$, $PCl_3$, $PCl_5$, $POBr_3$, HF, and the like, with $POCl_3$ and $SOCl_2$ being preferred. The halogenation could be performed neat in the halogenating reagent, or in any organic solvent which does not react with the halogenating reagent, such as DME, diglyme, THF's, halocarbons and the like, with DME and THF's being preferred. The reaction temperature could be between −20° C. and 150° C. with 25° C. to 100° C. being preferred.

V. Preferred Embodiments of The Compound of Formula (I)

Preferred embodiments of the compounds of formula (I) that might be prepared by the process of the present invention include the embodiments set forth below.

Preferred embodiments include compounds of formula (I) as described above, wherein the cyclopropyl moiety on the right-hand side is selected from the 2 different diastereoisomers where the 1-carbon center of the cyclopropyl has the R configuration as represented by exemplary structures (i) and (ii):

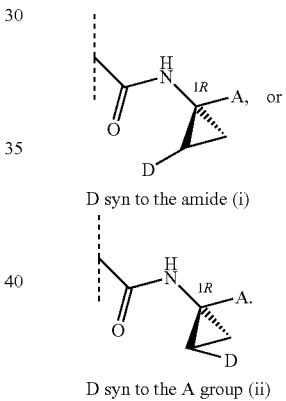

D syn to the amide (i)

D syn to the A group (ii)

In one specific embodiment of the compounds of formula (I), the D linker is in the configuration syn to the A group as represented by structure (ii) above;

W is N;

$L^0$ is selected from H, —OH, —$OCH_3$, —$OC_2H_5$, —$OC_3H_7$, —$OCH(CH_3)_2$, —$NHCH_3$, —$NHC_2H_5$, —$NHC_3H_7$, —$NHCH(CH_3)_2$, —$N(CH_3)_2$, —$N(CH_3)C_2H_5$, —$N(CH_3)C_3H_7$ and —$N(CH_3)CH(CH_3)_2$.

$L^1$ and $L^2$ are each independently selected from hydrogen, fluorine, chlorine, bromine, —$CH_3$, —$C_2H_5$, —$C_3H_7$, —$CH(CH_3)_2$, —$OCH_3$, —$OC_2H_5$, —$OC_3H_7$ and —$OCH(CH_3)_2$, $R^2$ is H, $C_{1-6}$ thioalkyl, $C_{1-6}$ alkoxy, phenyl or Het selected from the following:

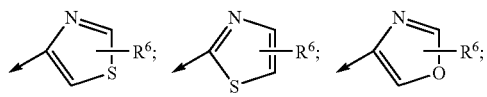

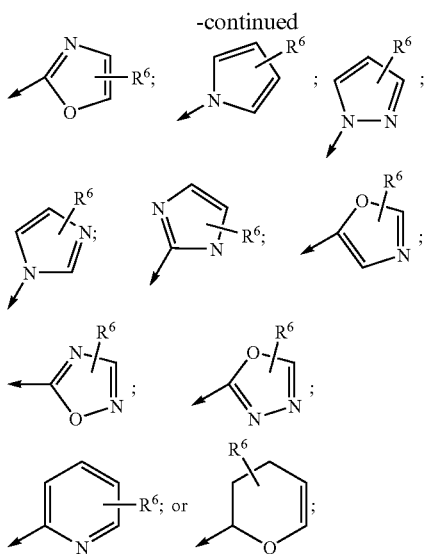

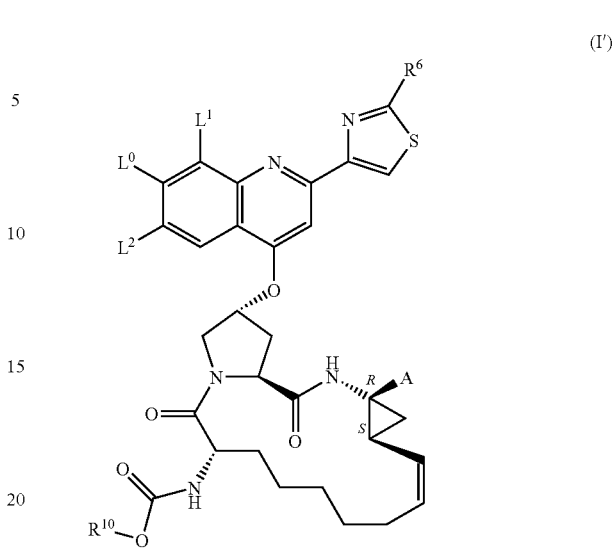

wherein $R^6$ is H, $C_{1-6}$ alkyl, NH—$R^7$, NH—C(O)—$R^7$, NH—C(O)—NH—$R^7$, wherein each $R^7$ is independently: H, $C_{1-6}$ alkyl, or $C_{3-6}$ cycloalkyl;

or $R^6$ is NH—C(O)—O$R^8$, wherein $R^8$ is $C_{1-6}$ alkyl;

$R^3$ is NH—C(O)—$R^{10}$, NH—C(O)—O$R^{10}$ or NH—C(O)—N$R^{10}$, wherein in each case $R^0$ is $C_{1-6}$ alkyl, or $C_{3-6}$ cycloalkyl; and D is a 6 to 8-atom unsaturated alkylene chain;

$R^4$ is H or $C_{1-6}$ alkyl;

and A is a carboxylic acid or a pharmaceutically acceptable salt or ester thereof.

In another specific embodiment of the compounds of formula (I), the D linker is in the configuration syn to the A group as represented by structure (ii) above;

W is N;

$L^0$ is selected from H, —OH, —OCH$_3$ and —N(CH$_3$)$_2$;

one of $L^1$ and $L^2$ is —CH$_3$, —F, —Cl or —Br and the other of $L^1$ and $L^2$ is H, or both $L^1$ and $L^2$ are H;

$R^2$ is

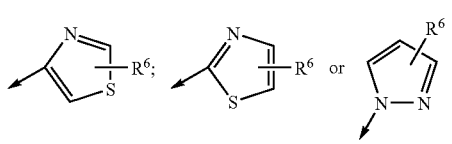

wherein $R^6$ is NH—R or NH—C(O)—$R^7$, wherein $R^7$ is independently: $C_{1-6}$ alkyl, or $C_{3-6}$ cycloalkyl;

$R^3$ is NH—C(O)—O$R^{10}$, wherein $R^{10}$ is $C_{1-6}$ alkyl, or $C_{3-6}$ cycloalkyl;

$R^4$ is H or $C_{1-6}$ alkyl;

D is a 7-atom unsaturated alkylene chain having one double bond; and

A is a carboxylic acid or a pharmaceutically acceptable salt or ester thereof.

In another specific embodiment, the compounds of formula (I) have the formula (I') below:

$L^0$ is —OCH$_3$;

$L^1$ is —CH$_3$, —F, —Cl or —Br and and $L^2$ is H, or both $L^1$ and $L^2$ are H;

$R^6$ is NH—$R^7$ or NH—C(O)—$R^7$, wherein $R^7$ is independently: $C_{1-6}$ alkyl or $C_{3-6}$ cycloalkyl;

$R^{10}$ is butyl, cyclobutyl or cyclopentyl;

A is a carboxylic acid or a pharmaceutically acceptable salt or ester thereof.

The following table lists compounds representative of the compounds of formula (I). A compound of the formula below:

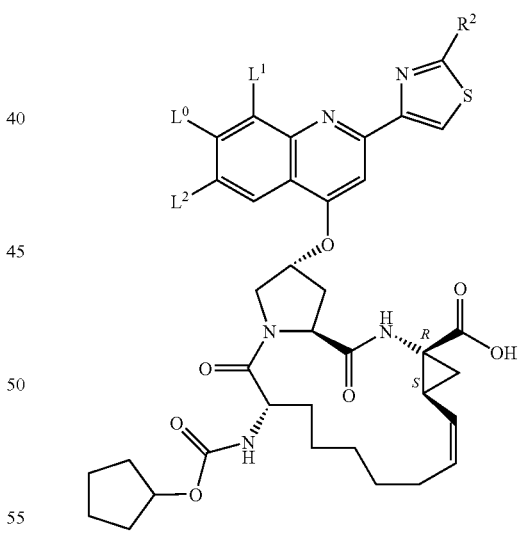

wherein $L^0$, $L^1$, $L^2$ and $R^2$ are as defined below:

| Cpd # | $L^2$ | $L^0$ | $L^1$ | $R^2$ |
|---|---|---|---|---|
| 101 | H | —OMe | Me |  |

-continued

| Cpd # | L² | L⁰ | L¹ | R² |
|---|---|---|---|---|
| 102 | H | —OMe | Me | *NHC(O)CH₃* |
| 103 | H | —OMe | Me | *NHC(O)CH(CH₃)₂* |
| 104 | H | —OMe | Me | *NHC(O)CH₂CH₃* |
| 105 | H | —OMe | Br | *NHC(O)CH₂CH₃* |
| 106 | H | —OMe | Br | *NH-iPr* |
| 107 | H | —OMe | Cl | *NH-iPr* |
| 108 | H | —OMe | Cl | *NHC(O)CH₂CH₃* |
| 109 | Me | —OMe | Me | *NH-iPr* |
| 110 | Me | —OMe | Me | *NHC(O)CH₂CH₃* |
| 111 | H | —OMe | F | *NH-iPr* |
| 112 | H | —OMe | F | *NHC(O)CH₂CH₃* |
| 113 | H | —OMe | Cl | *NHC(O)CH₂CH₂CH₃* |
| 114 | H | —OMe | Br | *NHC(O)CH₂CH₂CH₃* |
| 115 | H | —OMe | Br | *NHC(O)CH(CH₃)₂* |
| 116 | H | —OMe | Br | *NHC(O)OCH(CH₃)₂* |

The following table list additional compounds representative of the compounds of formula (I). A compound of the formula below:

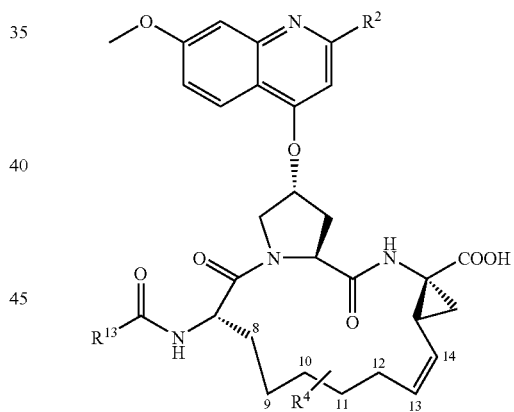

wherein the bond from position 14 to the cyclopropyl group is syn to the COOH, said 13,14 double bond is cis, $R^{13}$, $R^4$ and $R^2$ are defined as follows:

| Cpd # | R¹³: | R⁴: | R²: |
|---|---|---|---|
| 201 | cyclobutyloxy | H | 2-(acetylamino)thiazol-4-yl |

-continued

| Cpd # | R¹³ | R⁴ | R² |
|---|---|---|---|
| 202 | (S)-tBuCH(Me)NH- | H | 2-(acetylamino)thiazol-4-yl |
| 203 | cyclopentyl-O- | H | pyrrol-1-yl |
| 204 | cyclopentyl-O- | H | OEt |
| 205 | isopropyl-O- | H | OEt |
| 206 | cyclopentyl-O- | H | 2-(acetylamino)thiazol-4-yl |
| 207 | cyclopentyl-O- | H | 2-(ethylamino)thiazol-4-yl |
| 208 | cyclopentyl-O- | H | 2-(methylamino)thiazol-4-yl |
| 209 | cyclopentyl-O- | H | 2-aminothiazol-4-yl |
| 210 | cyclopentyl-O- | H | thiazol-2-yl |
| 211 | cyclopentyl-O- | H | 6-methylpyridin-2-yl |
| 212 | (S)-tBuCH(Me)NH- | H | 2-(ethylamino)thiazol-4-yl |
| 213 | cyclopentyl-O- | H | 4-isopropylthiazol-2-yl |
| 214 | cyclopentyl-O- | H | 2-(methoxycarbonylamino)thiazol-4-yl |

-continued

| Cpd # | R¹³ | R⁴ | R² |
|---|---|---|---|
| 215 | cyclopentyl-O- | H | thiazol-4-yl-2-NH-C(=O)-O-CH₂CH(CH₃)₂ |
| 216 | cyclobutyl-O- | H | thiazol-4-yl-2-NH-ethyl |
| 217 | cyclopentyl-O- | H | pyrazol-1-yl |
| 218 | cyclopentyl-O- | H | thiazol-4-yl-2-NH-isopropyl |
| 219 | cyclopentyl-O- | H | 3-methylpyrazol-1-yl |
| 220 | cyclopentyl-O- | 10-(R) Me | OEt |
| 221 | cyclopentyl-O- | H | thiazol-4-yl-2-NH-cyclopropyl |
| 222 | cyclopentyl-O- | H | thiazol-4-yl-2-NH-cyclobutyl |
| 223 | cyclopentyl-O- | H | thiazol-4-yl-2-NH-cyclopentyl |
| and 224 | cyclopentyl-O- | H | thiazol-4-yl-2-NH-cyclohexyl |

Additional specific compounds that are representative of the compounds of formula (I) may be found in U.S. Pat. No. 6,608,027 B1.

VI. Preferred Embodiments of The Compound of Formula QUIN

Preferred embodiments of the compounds of formula QUIN that might be used in the process of the present invention include the embodiments set forth below, i.e., those corresponding to the preferred embodiments of formula (I) compounds described above.

In one embodiment of the compounds of formula QUIN:

W is N;

$L^0$ is selected from H, —OH, —OCH₃, —OC₂H₅, —OC₃H₇, —OCH(CH₃)₂, —NHCH₃, —NHC₂H₅, —NHC₃H₇, —NHCH(CH₃)₂, —N(CH₃)₂, —N(CH₃)C₂H₅, —N(CH₃)C₃H₇ and —N(CH₃)CH(CH₃)₂.

$L^1$ and $L^2$ are each independently selected from hydrogen, fluorine, chlorine, bromine, —CH₃, —C₂H₅, —C₃H₇, —CH(CH₃)₂, —OCH₃, —OC₂H₅, —OC₃H₇ and —OCH(CH₃)₂, $R^2$ is $C_{1-6}$ thioalkyl, $C_{1-6}$ alkoxy, or Het selected from the following:

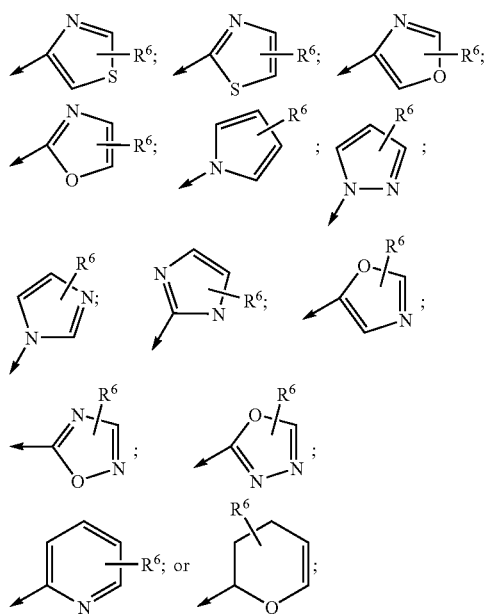

wherein $R^6$ is H, $C_{1-6}$ alkyl, NH—$R^7$, NH—C(O)—$R^7$, NH—C(O)—NH—$R^7$, wherein each $R^7$ is independently: H, $C_{1-6}$ alkyl, or $C_{3-6}$ cycloalkyl;
or $R^6$ is NH—C(O)—O$R^8$, wherein $R^8$ is $C_{1-6}$ alkyl;
and R is an $C_6$ or $C_{10}$ aryl group.

In another specific embodiment of the compounds of formula QUIN:
W is N;
$L^0$ is selected from H, —OH, —OCH$_3$ and —N(CH$_3$)$_2$;
one of $L^1$ and $L^2$ is —CH$_3$, —F, —Cl or —Br and the other of $L^1$ and $L^2$ is H, or both $L^1$ and $L^2$ are H;
$R^2$ is

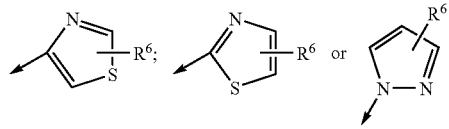

wherein $R^6$ is NH—$R^7$ or NH—C(O)—$R^7$, wherein $R^7$ is independently: $C_{1-6}$ alkyl, or $C_{3-6}$ cycloalkyl;
and R is a $C_6$ or $C_{10}$ aryl group.

In another specific embodiment, the compounds of formula QUIN have the formula below:

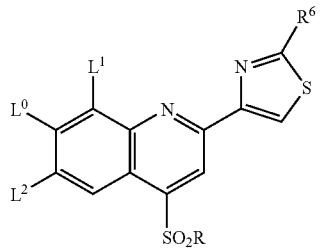

$L^0$ is —OCH$_3$;
$L^1$ is —CH$_3$, —F, —Cl or —Br and $L^2$ is H, or both $L^1$ and $L^2$ are H;
$R^6$ is NH—$R^7$ or NH—C(O)—$R^7$ wherein $R^7$ is independently: $C_{1-6}$ alkyl or $C_{3-6}$ cycloalkyl;
and R is a $C_6$ or $C_{10}$ aryl group.

The following table lists compounds representative of the compounds of formula QUIN. A compound of the formula below:

![compound structure with L0, L1, L2, R2, SO2Ph]

wherein Ph is phenyl and $L^0$, $L^1$, $L^2$ and $R^2$ are as defined below:

| Cpd # | $L^2$ | $L^0$ | $L^1$ | $R^2$ |
|-------|-------|-------|-------|-------|
| 301 | H | —OMe | Me | NH-iPr |
| 302 | H | —OMe | Me | NHC(O)Me |
| 303 | H | —OMe | Me | NHC(O)iPr |
| 304 | H | —OMe | Me | NHC(O)Et |
| 305 | H | —OMe | Br | NHC(O)Et |
| 306 | H | —OMe | Br | NH-iPr |
| 307 | H | —OMe | Cl | NH-iPr |
| 308 | H | —OMe | Cl | NHC(O)Et |
| 309 | Me | —OMe | Me | NH-iPr |

-continued

| Cpd # | L² | L⁰ | L¹ | R² |
|---|---|---|---|---|
| 310 | Me | —OMe | Me | N-propionyl (NHC(O)Et) |
| 311 | H | —OMe | F | NH-isopropyl |
| 312 | H | —OMe | F | NHC(O)Et |
| 313 | H | —OMe | Cl | NHC(O)Pr |
| 314 | H | —OMe | Br | NHC(O)Pr |
| 315 | H | —OMe | Br | NHC(O)iPr |
| 316 | H | —OMe | Br | NHC(O)OiPr |

The following table list additional compounds representative of the compounds of formula QUIN. A compound of the formula below:

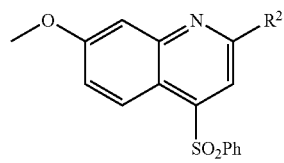

wherein Ph is phenyl and R² is as defined as follows:

| Cpd # | R² |
|---|---|
| 401 | 4-(2-acetamido-thiazolyl) |
| 402 | 4-(2-acetamido-thiazolyl) |
| 403 | N-pyrrolyl |
| 404 | OEt; |
| 405 | OEt; |
| 406 | 4-(2-acetamido-thiazolyl) |
| 407 | 4-(2-ethylamino-thiazolyl) |
| 408 | 4-(2-amino-thiazolyl, N-methyl) |
| 409 | 4-(2-amino-thiazolyl) |
| 410 | 2-thiazolyl |
| 411 | 6-methyl-2-pyridyl |
| 412 | 4-(2-ethylamino-thiazolyl) |
| 413 | 4-isopropyl-2-thiazolyl |
| 414 | 4-(2-methoxycarbonylamino-thiazolyl) |
| 415 | 4-(2-isobutoxycarbonylamino-thiazolyl) |
| 416 | 4-(2-ethylamino-thiazolyl) |

-continued

| Cpd # | R² |
|---|---|
| 417 | 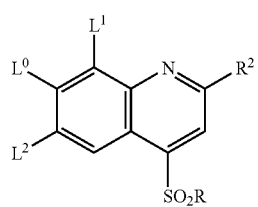 |
| 418 | |
| 419 | |
| 420 | OEt; |
| 421 | |
| 422 | |
| 423 | |
| and 424 | |

We claim:

1. A compound of the following formula QUIN:

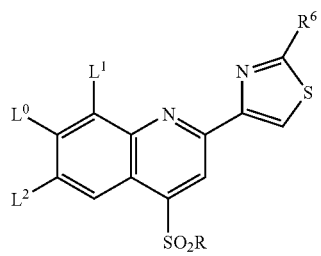

QUIN wherein:
- $L^0$ selected from H, —OH, —OCH$_3$, —OC$_2$H$_5$, —OC$_3$H$_7$, —OCH(CH$_3$)$_2$, —NHCH$_3$, —NHC$_2$H$_5$, —NHC$_3$H$_7$, —NHCH(CH$_3$)$_2$, —N(CH$_3$)$_2$, —N(CH$_3$)C$_2$H$_5$, —N(CH$_3$)C$_3$H$_7$ and —N(CH$_3$)CH(CH$_3$)$_2$;
- $L^1$ and $L^2$ are each independently selected from hydrogen, fluorine, chlorine, bromine, —CH$_3$, —C$_2$H$_5$, —C$_3$H$_7$, —CH(CH$_3$)$_2$, —OCH$_3$, —OC$_2$H$_5$, —OC$_3$H$_7$ and —OCH(CH$_3$)$_2$;
- $R^2$ is C$_{1-6}$ thioalkyl, C$_{1-6}$ alkoxy, or Het, where Het is selected from the following:

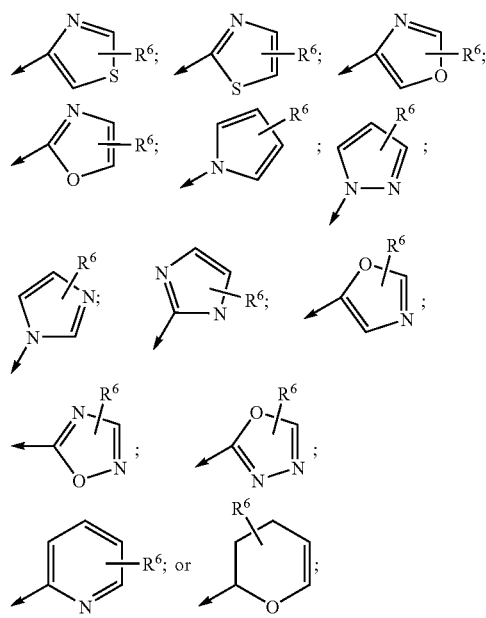

wherein $R^6$ is H, C$_{1-6}$ alkyl, NH—R$^7$, NH—C(O)—R$^7$, or NH—C(O)—NH—R$^7$,
wherein each $R^7$ is independently: H, C$_{1-6}$ alkyl, or C$_{3-6}$ cycloalkyl;
or $R^6$ is NH—C(O)—OR$^8$, wherein R$^8$ is C$_{1-6}$ alkyl;
and R is a C$_6$ or C$_{10}$ aryl group.

2. A compound according to claim 1, wherein:
- $L^0$ is selected from H, —OH, —OCH$_3$ and —N(CH$_3$)$_2$;
- one of $L^1$ and $L^2$ is —CH$_3$, —F, —Cl or —Br and the other of $L^1$ and $L^2$ is H, or both $L^1$ and $L^2$ are H;
- $R^2$ is

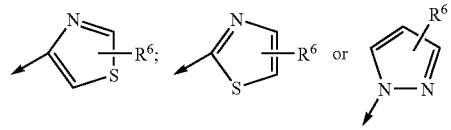

wherein $R^6$ NH—R$^7$ NH—C(O)—R$^7$, wherein R$^7$ is independently: C$_{1-6}$ alkyl, or C$_{3-6}$ cycloalkyl;
and R is a C$_6$ or C$_{10}$ aryl group.

3. A compound according to claim 2, having the following formula:

wherein:
- $L^0$ is —OCH$_3$;
- $L^1$ is —CH$_3$, —F, —Cl or —Br and $L^2$ is H, or both $L^1$ and $L^2$ are H;
- $R^6$ is NH—R$^7$ or NH—C(O)—R$^7$, wherein R$^7$ is independently: C$_{1-6}$ alkyl or C$_{3-6}$ cycloalkyl;
- and R is a C$_6$ or C$_{10}$ aryl group.

4. A process for preparing a compound of formula QUIN according to claim 1, said process comprising:

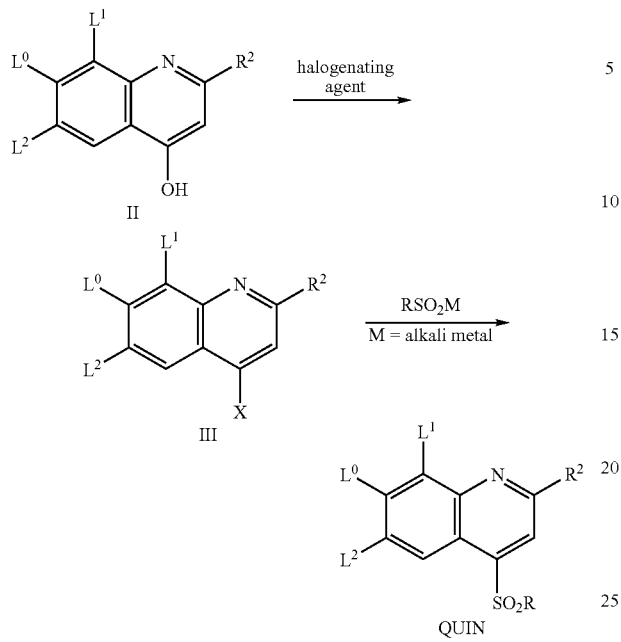

reacting a compound II with a halogenating agent to obtain a compound of formula III wherein X is a halogen atom, and then reacting a compound of formula III with a sulfinate salt $RSO_2M$, wherein M is an alkali metal, to obtain a compound QUIN, and wherein $L^0$, $L^1$, $L^2$, $R^2$ and R are as defined in claim 1.

5. A process according to claim 4, wherein the halogenating agent is selected from $POX_3$ and $PX_5$, where X=F, Cl, Br or I, and wherein the sulfinate salt $RSO_2M$ is $PhSO_2Na$.

6. A process for preparing a compound of formula QUIN according to claim 1, said process comprising:

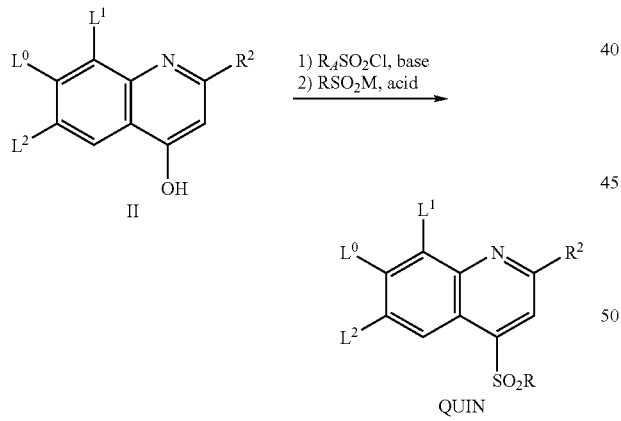

reacting a compound II with an arene sulfonylchloride compound $R_ASO_2Cl$, wherein $R_A$ is a neutral or electron rich arene group, in the presence of a suitable base in a suitable solvent, and then reacting the resulting compound in the presence of an acid with a sulfinate salt $RSO_2M$, wherein M is an alkali metal, to obtain a compound QUIN, and wherein $L^0$, $L^1$, $L^2$, $R^2$ and R are as defined in claim 1.

7. A process according to claim 6, wherein in the first step the arene sulfonylchloride compound $R_ASO_2Cl$ is benzenesulfonyl chloride or tosyl chloride, the base is N-methylpyrrolidine or diisopropylethylamine, and the solvent is selected from acetonitrile, THF, toluene and DMF; and in the second step the acid is acetic acid, trifluoroacetic acid or hydrochloric acid and the sulfinate salt $RSO_2M$ is $PhSO_2Na$, $PhSO_2K$ or $PhSO_2Cs$.

8. A process according to claim 7, wherein the arene sulfonylchloride compound $R_ASO_2Cl$ is benzenesulfonyl chloride, the base is N-methylpyrrolidine, the solvent is acetonitrile, the acid is acetic acid and sulfinate salt $RSO_2M$ is $PhSO_2Na$.

9. A compound according to claim 1, which is selected from the compounds of the following formula:

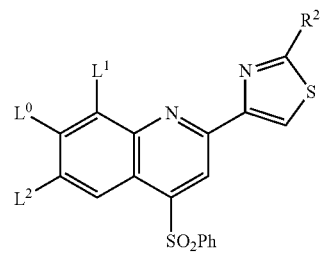

wherein Ph is phenyl and $L^0$, $L^1$, $L^2$ and $R^2$ are:

| Cpd # | $L^2$ | $L^0$ | $L^1$ | $R^2$ |
|---|---|---|---|---|
| 301 | H | —OMe | Me | ⸺NH-iPr |
| 302 | H | —OMe | Me | ⸺NHC(O)CH₃ |
| 303 | H | —OMe | Me | ⸺NHC(O)CH(CH₃)₂ |
| 304 | H | —OMe | Me | ⸺NHC(O)CH₂CH₃ |
| 305 | H | —OMe | Br | ⸺NHC(O)CH₂CH₃ |
| 306 | H | —OMe | Br | ⸺NH-iPr |
| 307 | H | —OMe | Cl | ⸺NH-iPr |
| 308 | H | —OMe | Cl | ⸺NHC(O)CH₂CH₃ |

-continued
| Cpd # | L² | L⁰ | L¹ | R² |
|---|---|---|---|---|
| 309 | Me | —OMe | Me | 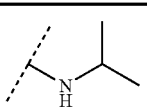 |
| 310 | Me | —OMe | Me | 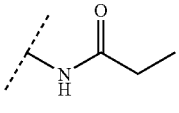 |
| 311 | H | —OMe | F | 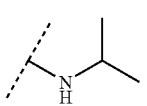 |
| 312 | H | —OMe | F | 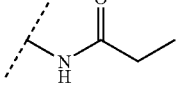 |
| 313 | H | —OMe | Cl | 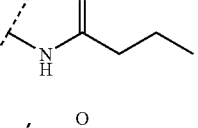 |
| 314 | H | —OMe | Br | 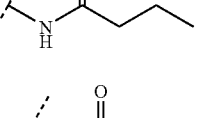 |
| 315 | H | —OMe | Br | 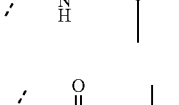 |
| 316 | H | —OMe | Br | 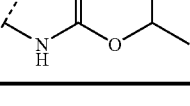 |
10. A compound according to claim 1, which is selected from the compounds of the following formula:
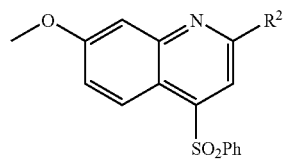
wherein Ph is phenyl and R² is:
| Cpd # | R² |
|---|---|
| 401 | 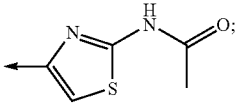 |
-continued
| Cpd # | R² |
|---|---|
| 402 | 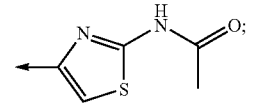 |
| 403 | 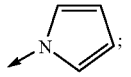 |
| 404 | OEt; |
| 405 | OEt; |
| 406 | 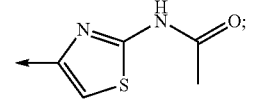 |
| 407 | 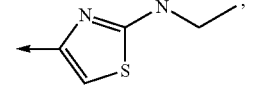 |
| 408 | 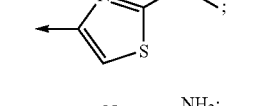 |
| 409 | 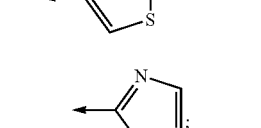 |
| 410 | 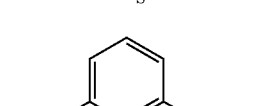 |
| 411 | 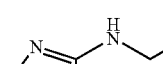 |
| 412 | 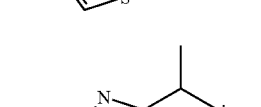 |
| 413 | 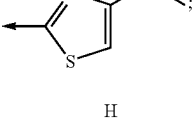 |
| 414 | 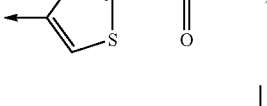 |
| 415 | 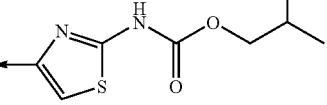 |

-continued

| Cpd # | R² |
|---|---|
| 416 | 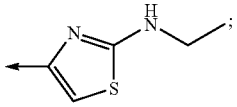 |
| 417 | 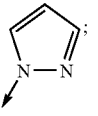 |
| 418 | 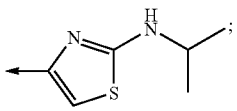 |
| 419 | 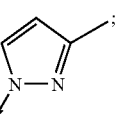 |
| 420 | OEt; |
| 421 | 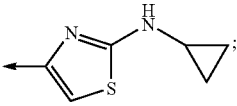 |
| 422 | 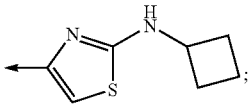 |

-continued

| Cpd # | R² |
|---|---|
| 423 | 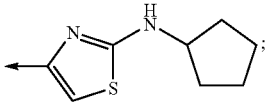 |
| and 424 | 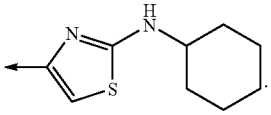 |

11. A compound according to claim 9, which is Cpd #301.
12. A compound according to claim 9, which is Cpd #302.
13. A compound according to claim 9, which is Cpd #303.
14. A compound according to claim 9, which is Cpd #304.
15. A compound according to claim 9, which is Cpd #305.
16. A compound according to claim 9, which is Cpd #306.
17. A compound according to claim 9, which is Cpd #307.
18. A compound according to claim 9, which is Cpd #308.
19. A compound according to claim 9, which is Cpd #309.
20. A compound according to claim 9, which is Cpd #310.
21. A compound according to claim 9, which is Cpd #311.
22. A compound according to claim 9, which is Cpd #312.
23. A compound according to claim 9, which is Cpd #313.
24. A compound according to claim 9, which is Cpd #314.
25. A compound according to claim 9, which is Cpd #315.
26. A compound according to claim 9, which is Cpd #316.

\* \* \* \* \*

UNITED STATES PATENT AND TRADEMARK OFFICE
CERTIFICATE OF CORRECTION

| | | |
|---|---|---|
| PATENT NO. | : 7,608,614 B2 | Page 1 of 1 |
| APPLICATION NO. | : 11/276573 | |
| DATED | : October 27, 2009 | |
| INVENTOR(S) | : Busacca et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 334 days Delete the phrase "by 334 days" and insert -- by 516 days --

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,608,614 B2  Page 1 of 1
APPLICATION NO. : 11/276573
DATED : October 27, 2009
INVENTOR(S) : Busacca et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 698 days.

Signed and Sealed this

Twelfth Day of October, 2010

David J. Kappos
*Director of the United States Patent and Trademark Office*